United States Patent [19]

Sloane, Jr. et al.

[11] 4,294,594

[45] Oct. 13, 1981

[54] SELF-CONTAINED FILTER ASSEMBLY FOR REMOVING AIR, PARTICLES AND BACTERIA FROM A SOLUTION

[75] Inventors: Thomas E. Sloane, Jr., West Redding; Clair Melius, Southport, both of Conn.; Erich Kling, Carmel, N.Y.

[73] Assignee: United States Surgical Corporation, Norwalk, Conn.

[21] Appl. No.: 81,185

[22] Filed: Oct. 2, 1979

[51] Int. Cl.³ .................... B01D 25/00; B01D 53/22
[52] U.S. Cl. .......................... 55/186; 55/199; 128/214 R; 210/436; 210/446; 210/497.01; 210/927
[58] Field of Search .................. 55/35, 74, 97, 159, 55/171, 185, 186, 199; 128/214 R, 214 C, 214.2; 204/301; 210/94, 136, 321 A, 344, 435, 436, 446-448, 455, 497 R, DIG. 23

[56] References Cited

U.S. PATENT DOCUMENTS

| | | | |
|---|---|---|---|
| 2,741,595 | 4/1956 | Juda | 204/301 |
| 3,066,462 | 12/1962 | Yap et al. | 55/97 |
| 3,252,270 | 5/1966 | Pall et al. | 55/74 |
| 3,300,949 | 1/1967 | Smylie et al. | 55/35 |
| 3,306,459 | 2/1967 | Bush | 210/344 |
| 3,359,977 | 12/1967 | Burke | 128/214 R |
| 3,364,658 | 1/1968 | Walker | 55/171 |
| 3,388,803 | 6/1968 | Scott | 210/321 A |
| 3,471,019 | 10/1969 | Trasen et al. | 210/94 |
| 3,523,408 | 8/1970 | Rosenberg | 55/159 |
| 3,631,654 | 1/1972 | Riely et al. | 55/159 |
| 3,650,093 | 3/1972 | Rosenberg | 55/159 |
| 3,674,147 | 7/1972 | Danti | 210/136 |
| 3,701,433 | 10/1972 | Krakauer et al. | 128/214 C X |
| 3,722,696 | 3/1973 | Dwyer et al. | 210/497 X |
| 3,726,407 | 4/1973 | Weyand | 210/497 X |
| 3,730,535 | 5/1973 | Trasen et al. | 310/455 |
| 3,778,971 | 12/1973 | Granger et al. | 55/159 |
| 3,778,973 | 12/1973 | Martinez | 55/199 |
| 3,803,810 | 4/1974 | Rosenberg | 55/159 |
| 3,827,562 | 8/1974 | Esmond | 128/214 R X |
| 3,834,124 | 9/1974 | Ichikawa | 55/159 |
| 3,854,907 | 12/1974 | Rising | 55/159 |
| 3,905,905 | 9/1975 | O'Leary et al. | 55/159 X |
| 3,962,097 | 6/1976 | Reiman et al. | 210/435 |
| 4,004,587 | 1/1977 | Jess | 55/159 X |
| 4,009,714 | 3/1977 | Hammer | 128/214 R |
| 4,009,715 | 3/1977 | Forberg et al. | 128/214 R |
| 4,021,353 | 5/1977 | Raines et al. | 128/214 R X |
| 4,031,891 | 6/1977 | Jess | 128/214 R |
| 4,080,294 | 3/1978 | Edwards et al. | 210/436 X |
| 4,113,627 | 9/1978 | Leason | 128/214 R X |
| 4,116,646 | 9/1978 | Edwards | 55/159 |
| 4,177,149 | 12/1979 | Rosenberg | 55/159 X |
| 4,188,948 | 2/1980 | Swinton | 55/159 X |
| 4,190,426 | 2/1980 | Ruschke | 55/185 |

FOREIGN PATENT DOCUMENTS 1221625 2/1971 United Kingdom .................. 55/159

Primary Examiner—Robert H. Spitzer
Attorney, Agent, or Firm—Fleit & Jacobson

[57] ABSTRACT

A filter assembly for removing particulate matter, bacteria and air from a liquid. The filter assembly comprises a housing having an inlet for receiving the liquid within the housing and an outlet to provide an exit for the liquid. All of the liquid entering the housing passes through a primary filtration stage that contains a hydrophobic filter arrangement for venting air in the liquid to the atmosphere and a depth filter arrangement for filtering particulate matter in the liquid. Alo disposed in the housing is a secondary filtration stage through which all of the liquid passes after leaving the primary filtration stage. The secondary filtration stage includes a hydrophobic filter arrangement for venting any remaining air in the liquid to the atmosphere and a final filter for removing bacteria from the liquid.

15 Claims, 16 Drawing Figures

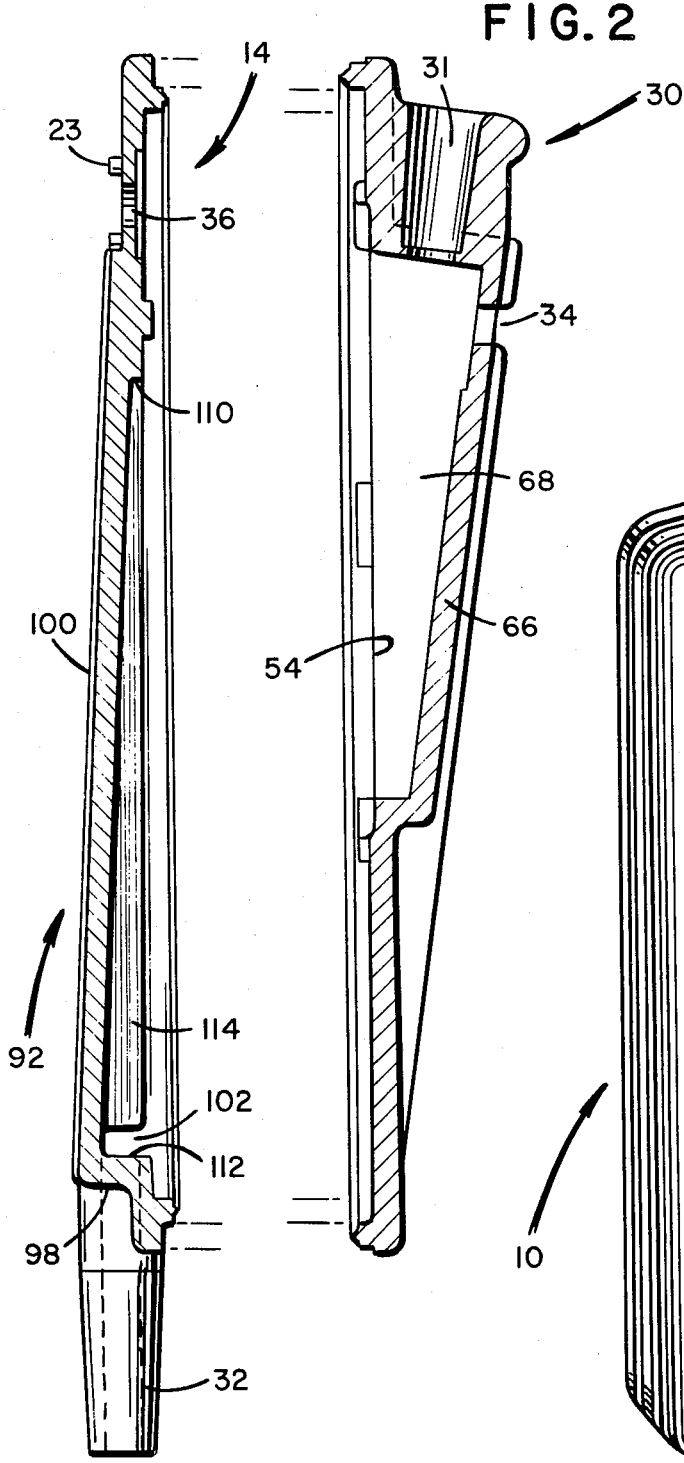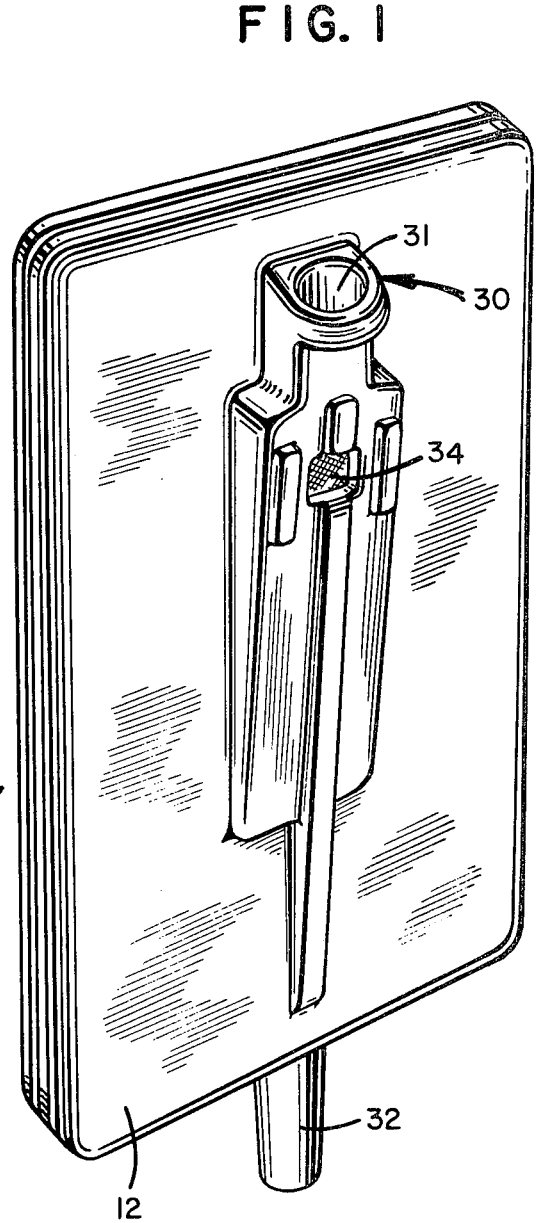

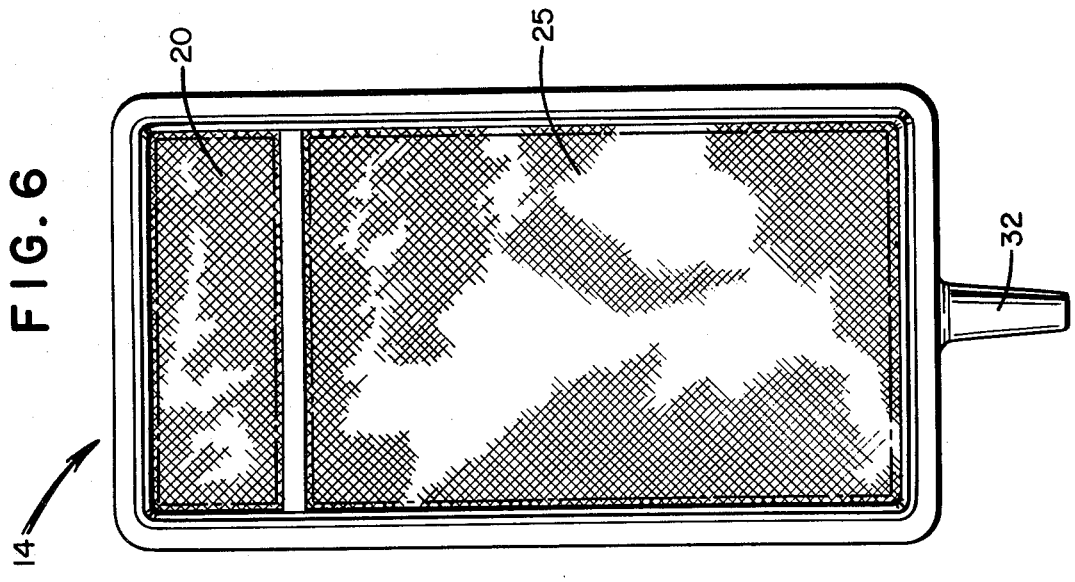
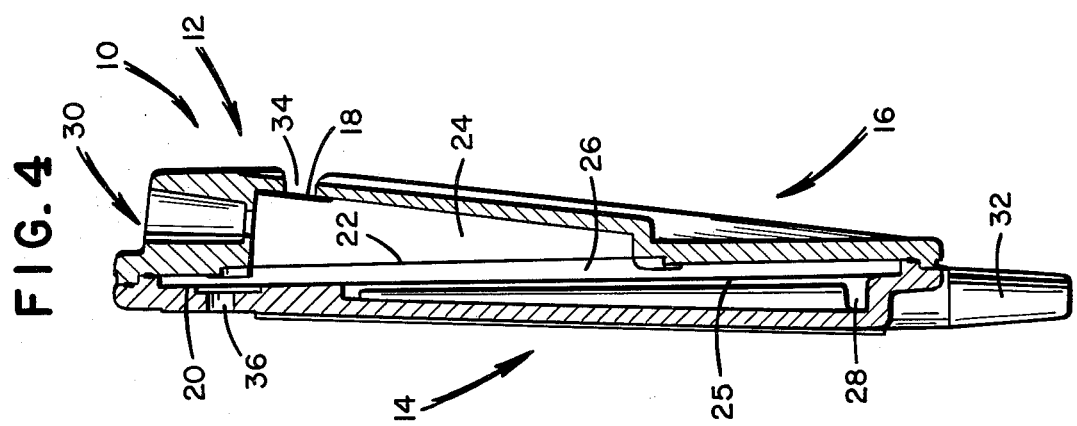
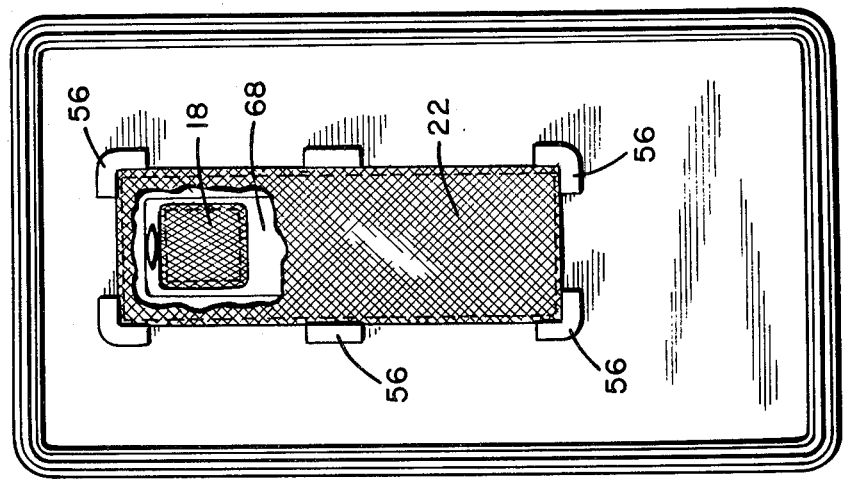

SELF-CONTAINED FILTER ASSEMBLY FOR REMOVING AIR, PARTICLES AND BACTERIA FROM A SOLUTION

BACKGROUND OF THE INVENTION

1. Field of the Invention

This invention relates to filters, in general, and to a self-contained filter assembly for removing air, particles, and bacteria from a solution, in particular.

2. Description of the Prior Art

In the intravenous adminstration of liquid medications, parenteral solutions and the like, it is absolutely necessary that the solution being administered into a patient be free of entrained air, particulate matter, and bacteria. The prior art has come up with various filter arrangements to solve the problems associated with the removal of air entrained in a parenteral solution and also the removal of particulate matter and bacteria.

One class of filters, used to vent the air entrapped in the parenteral solution, employ various combinations of hydrophobic and hydrophilic filters. A hydrophobic filter is one which allows the passage of gas but does not allow the passage of liquid. A hydrophilic filter is one which allows the passage of liquid but does not allow the passage of gas. As examples of this type of filter arrangement, the following patents are considered exemplary:

U.S. Pat. No. 3,523,408 (Rosenberg); U.S. Pat. No. 3,631,654 (Riely); U.S. Pat. No. 3,803,810 (Rosenberg); U.S. Pat. No. 3,854,907 (Rising); U.S. Pat. No. 4,004,587 (Jess); U.S. Pat. No. 4,031,891 (Jess); and U.S. Pat. No. 4,116,646 (Edwards).

In all of the devices disclosed in these patents, the air entrained in the solution is vented to the atmosphere by passage through a hydrophobic filter. At the same time, air is prevented from flowing with the solution into the patient by passing the fluid through a hydrophilic filter immediately prior to infusion in the patient.

While all of these devices have a tendency to remove particulate matter, in that the hydrophilic filter is generally of a pore rating of 0.3 microns or less, none of these devices provide a filter dedicated to the removal of particulate matter. In fact, it is a problem of the prior art filtration devices that the hydrophilic filters contained therein, because of their small pore size, often clog as they are loaded with particulate matter. In addition, even though many of the prior art devices are position insensitive, there is still the problem of limited access to the means for venting entrained air to the atmosphere. Finally, because of the delicate nature of the hydrophilic filters employed in the prior art filter assemblies, there is a danger that one of these filters could rupture thus introducing a fatal quantity of air into the patient and also breaching the sterility protection of the patient.

There is thus a need for a filter assembly that comprises a primary filtration stage which both removes particulate matter and also vents the air contained in the liquid, coupled with a secondary filtration stage which both removes bacteria and vents any air remaining in the liquid. The present invention is directed towards filling that need.

BRIEF SUMMARY OF THE INVENTION

The present invention is intended primarily for use in an intravenous system wherein it is necessary to remove air, particles and bacteria from the solution being administered. The present invention is directed to a filter assembly for accomplishing the removal of the undesirable elements and comprises first and second body parts which are joined together to form a housing containing four filters; the filters and housing, in turn, define three chambers.

The first and second filters are hydrophobic filters which allow a gas to pass but not a liquid. The third filter is a hydrophilic filter which allows a liquid to pass but not a gas. The fourth filter is a depth filter which allows both a liquid and gas to pass but does not allow particulate matter to pass. The depth filter is of sufficient pore rating to remove particulate matter which would otherwise clog the hydrophilic filter.

The four filters are arranged within the housing so that the first filter, the fourth filter and the first body part define a first chamber. The third filter and the second body part define a third chamber, while the second, third and fourth filters, and the first and second body parts define a second chamber.

The first chamber is in fluid communication with the second chamber via the fourth filter to define a primary filtration stage for removing particulate matter and for venting air entrained in the liquid being filtered. The second chamber is in fluid communication with the third chamber via the third filter to define a secondary filtration stage for removing bacteria and for venting any air remaining in the liquid being filtered. An inlet conduit provides a fluid passageway or entrance into the first chamber for a liquid, such as a parenteral solution, which contains varying amounts of particulate matter, bacteria and entrained air. An outlet conduit provides a fluid passageway or exit from the third chamber for the liquid from which the particulate matter, bacteria and air have been removed by the various filters.

The first body portion, which defines a portion of the housing, contains an air vent for venting to the atmosphere air passing through the first filter when the first chamber contains the parenteral solution. The second body portion, which defines another portion of the housing, contains a number of air vent apertures for venting to the atmosphere air passing through the second filter when the fluid is contained in the second chamber.

Both the first and second hydrophobic filters perform a secondary function in addition to air venting by having a lower yield strength than the third hydrophilic filter, such that, if excessive pressure is applied to the third filter, either or both of the first and second filters will rupture before the hydrophilic filter can rupture, thus providing a visible indication of a damaged filter without breaching the sterility protection of the patient. In addition, should there be an upstream disturbance in the filter assembly, the hydrophilic filter prevents air from entering the patient.

It is thus an object of the present invention to provide a filter assembly for use in eliminating air entrained in a solution.

It is another object of the present invention to provide a filter assembly for use in removing particulate matter from a solution.

It is a further object of the present invention to provide a self contained filter for use in an intravenous therapy set to remove air, particulate matter, and bacteria from a parenteral solution being administered.

It is yet a further object of the present invention to provide a filter assembly which contains a separate filter element dedicated to the removal of particulate matter.

It is still an object of the present invention to provide a filter having a primary filtration section for both removing particulate matter from a fluid and for venting to the atmosphere air contained in the fluid, coupled with a secondary filtration section for venting to the atmosphere any remaining air in the solution, while filtering out any bacteria contained in the solution.

It is yet another object of the present invention to provide a filter assembly employing hydrophobic and hydrophilic filters in which the hydrophobic filter has a lower yield strength than the hydrophilic filter, such that, if excessive pressure is applied to the hydrophilic filter, than the hydrophobic filter will rupture before the hydrophilic filter can rupture, thus providing a visable indication of a damaged filter without breaching the sterility protection of the patient.

It is still another object of the present invention to provide a filter having primary and secondary means for venting to the atmosphere air entrained in a fluid.

It is still a further object of the present invention to provide a filter assembly for use in intravenous therapy to eliminate air entrained in a parenteral solution.

These and other objects will become apparent from the following drawings and detailed description.

BRIEF DESCRIPTION OF THE DRAWINGS

FIG. 1 is a perspective view showing the inlet side of a filter assembly embodying the present invention.

FIG. 2 is a longitudinal section of one half of the filter assembly of FIG. 1.

FIG. 3 is a longitudinal section of the other half of the filter assembly of FIG. 1.

FIG. 4 is a longitudinal section of the filter assembly.

FIG. 5 is a plan view of the inside of the half shown in FIG. 2.

FIG. 6 is a plan view of the inside of the half shown in FIG. 3.

DETAILED DESCRIPTION OF THE DRAWINGS

Figure 7:
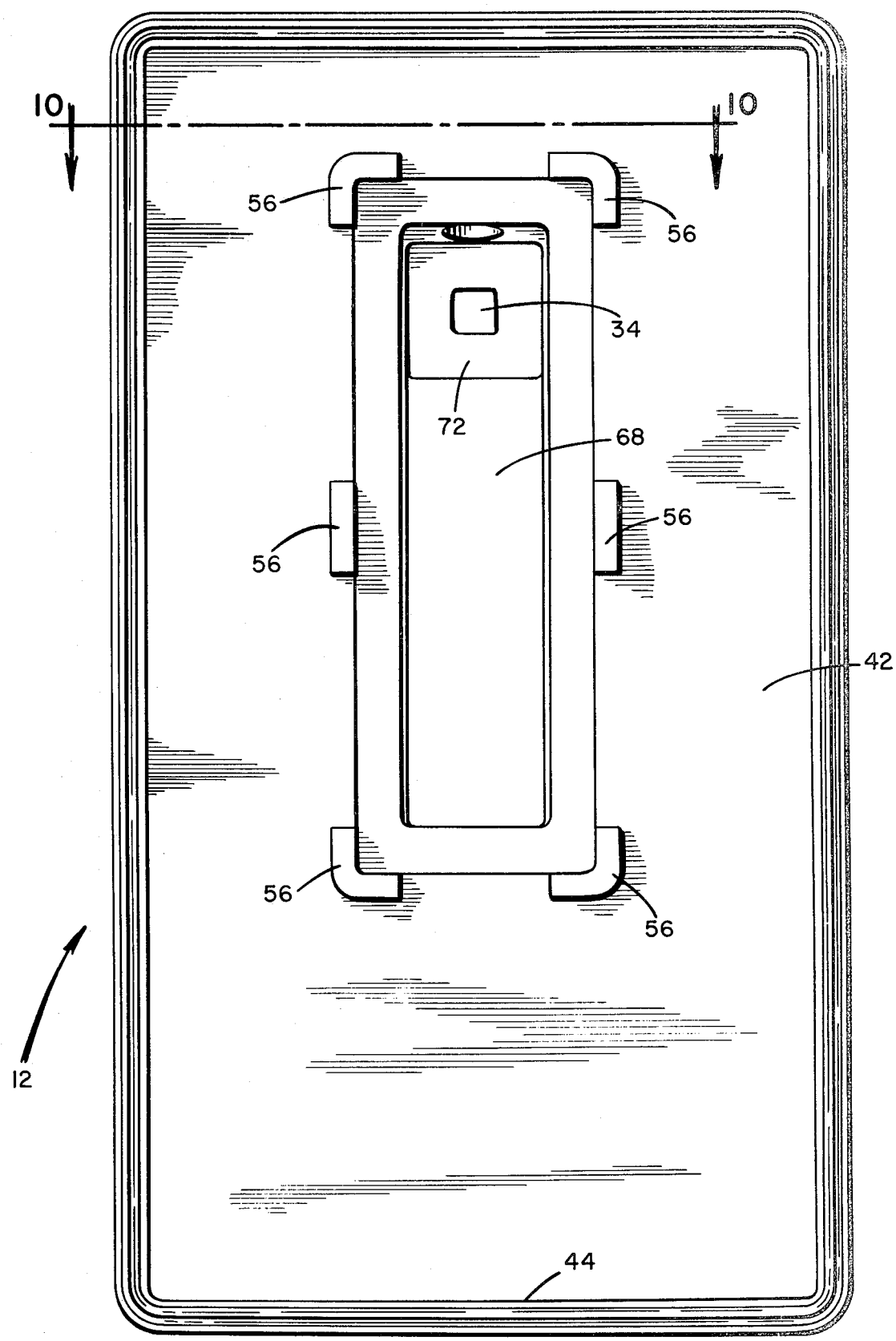
FIG. 7 is a plan view similar to FIG. 5, but with the filters removed.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

With reference to FIGS. 1–6 and 16, the filter, generally designated as 10, basically comprises a first body portion 12 and the second portion 14. The body portions 12 and 14 are tightly joined together about their perimeters to define housing 16. Two hydrophobic filters 18 and 20, a prefilter or depth filter 22, and a hydrophilic filter 25 are positioned within the housing and cooperate with the housing to define three chambers 24, 26 and 28. Inlet 30 is provided in the housing to allow fluid to enter the first chamber 24. An outlet 32 is provided in the housing to allow fluid to exit the third chamber 28.

When the filter 10 is in use, a fluid enters the inlet 30 to fill the chamber 24. The fluid contains liquid, particulate matter, bacteria and air. During priming, the filter is oriented as shown in FIG. 1 with the inlet at the top of the filter and the outlet located at the bottom of the filter. In this way, when the liquid, containing air, fills the chamber 24, the air has a tendency to rise and present itself to the hydrophobic filter 18. As it presents itself to the hydrophobic filter 18, the air is allowed to escape to the atmosphere through an air vent 34 provided within the housing. In this way, most, but possibly not all, of the air is removed from the liquid.

Figure 16:
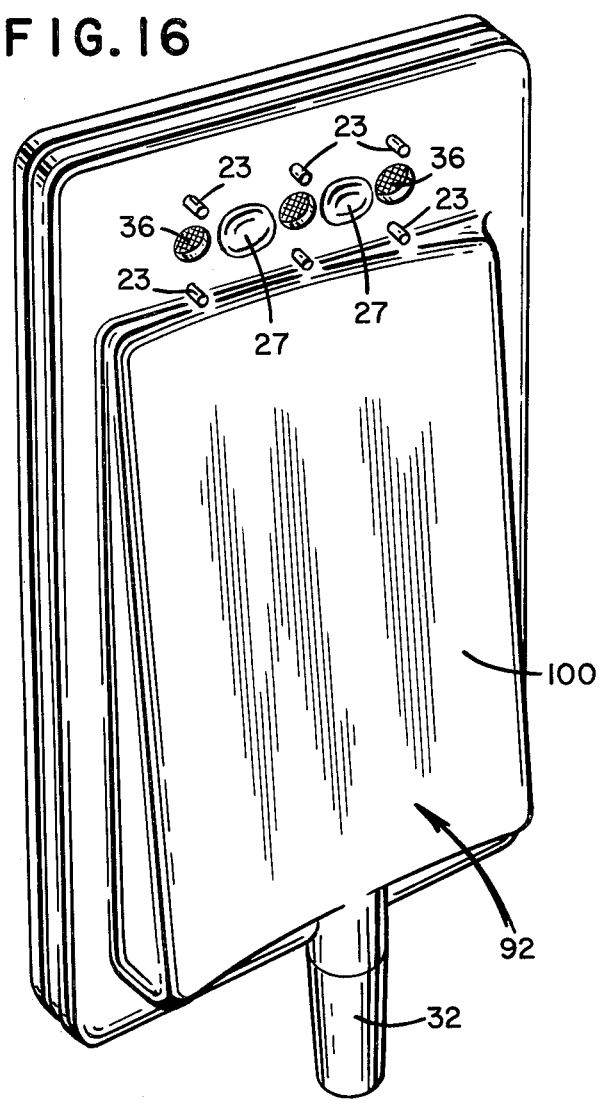
FIG. 16 is a perspective view showing the outlet side of the filter assembly of FIG. 1.

In use the filter 10 may hand vertically as in FIG. 1, or may be taped to a limb of a patient with the outlet 32 facing towards the hand or foot, as in FIG. 16. In addition, the filter may be positioned at any other location on the patient's body where the intravenous feeding is normally applied. After priming, when solution containing air enters inlet 30, the solution flows against the filter 34, and most of the air is removed regardless of the position of the filter.

The liquid, containing the particulate matter, bacteria, and, possibly still some air, then flows from chamber 24 to chamber 26 by passing through the prefilter 22 which is sized and shaped to remove particulate matter. It should be pointed out that the prefilter allows both the air and liquid to pass into chamber 26. When the chamber 26, the remaining air in the liquid rises to present itself to hydrophobic filter 20. As before, the air is allowed to pass to the atmosphere through vent holes 36 defined within the housing. The liquid wich is now free of air and particulate matter, travels from chamber 26 into chamber 28 after passing through a hydrophilic filter, which allows the liquid to pass but does not allow the air and bacteria to pass. The liquid contained in the chamber 28 exits from the filter through outlet 32. It is to be noted that, hydrophobic filter 20 also performs a function during priming of the filter 10. Since chamber 26 is filled with air before priming, hydrophobic filter 20 provides a means for the air to escape from the chamber during priming.

Each of the hydrophobic filters 18 and 20 has a secondary function other than the venting of air. Each hydrophobic filter has a lower yield strength than the hydrophilic filter 25, such that, if excessive pressure is applied to the hydrophilic filter 25, at least one of the hydrophobic filters 18 and 20 will rupture before the hydrophilic filter can rupture. Upon the rupturing of one of the hydrophobic filters, the liquid contained in the chamber associated with the ruptured filter will begin to leak out of the ruptured filter and associated air vent, thus providing a visible indication of a damaged filter assembly 10 without breaching the sterility protection of the patient. In addition, should there be an upstream disturbance in the filter assembly, the hydrophilic filter 25 prevents air from entering the patient.

A detailed description of the elements constituting the filter assembly 10 will now be presented.

With reference to FIGS. 2, 5, and 7–10, the first main body portion 12 comprises a generally elongated rectangular structure, preferably made from a clear plastic such as Richardson Crystal NAS 81. The main body portion 12 defines a generally planar outer surface 40 and a generally planar inner surface 42. A projection 44 circumscribes the entire periphery of the inner surface 42 and defines a margin 46.

The top surface 48 of the projection 44 terminates in an energy director 50 centrally located about the entire top surface 48. The energy director 50, when viewed in cross-section, is an equilateral triangle with its base in the plane of top surface 48.

In its orientation in FIG. 7, the inner surface 42 of the first body portion 12 contains a generally rectangular recessed ring 52 which surrounds an open area 54. The ring 52 is elongated in the same direction as the main body portion 12. At each of the outer corners of the ring 52 and along the outer portion, at approximately midway along the length of the ring 52 are guide projections 56, provided to faciliate the insertion of the prefilter 22 within the recess 52. The prefilter 22 is typically a depth filter of sufficient pore rating to remove particulate matter which would otherwise clog the hydrophilic filter 25. In addition, the filter should not resist the flow of air. With reference to FIG. 5, the prefilter 22 is secured to the recessed ring 52 in such a way so as to prevent any leaks at the filter-ring interface. One such way, which has proven to be very successful, is to employ ultrasonic welding.

The outer surface 40 of the body portion 12 contains a raised area generally designated as 60. The raised area is generally rectangular in shape and is defined by two side walls 62 and 64 and a cover wall 66. The two side walls and the cover wall, in turn, define an open space 68, within the raised area, which also is part of the open area 54. Looking at the filter as oriented in FIG. 2, the cover surface 66 is situated so that the space 68 gradually tapers as one moves away from the inlet. The reasons for this tapered structure are to keep the volume within the space 68 as small as possible and to promote maximum flow characteristics.

Figure 8:
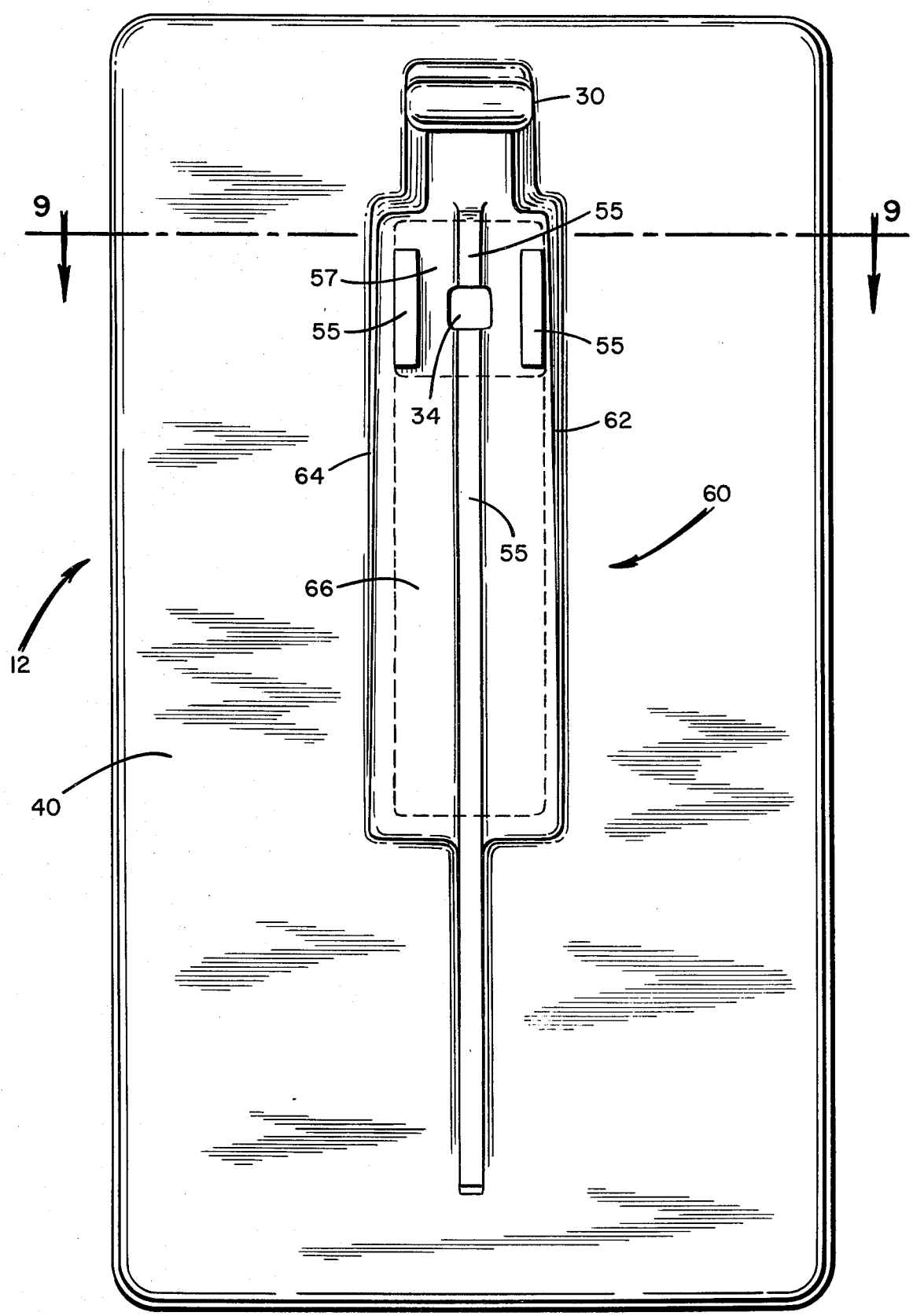
FIG. 8 is a plan view of the outside of the half shown in FIG. 5.
Figure 10:
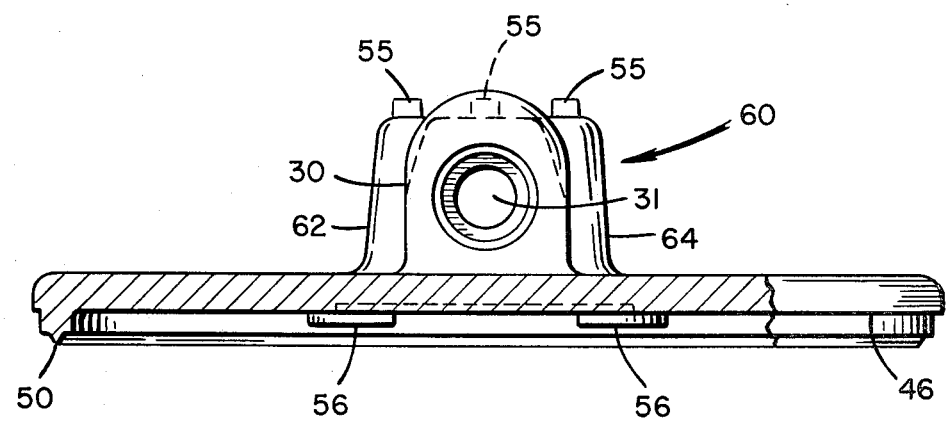
FIG. 10 is a part sectional view taken along lines 10—10 of FIG. 7.
Figure 9:
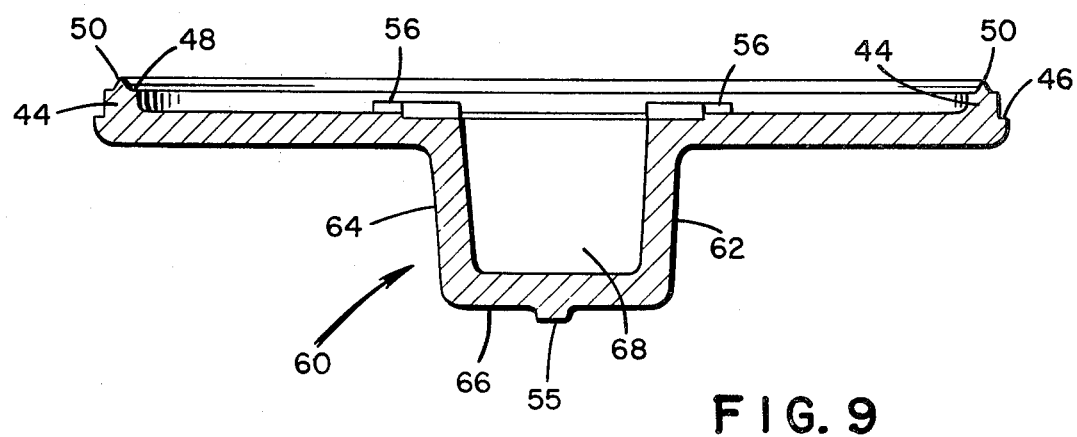
FIG. 9 is a sectional view taken along lines 9—9 of FIG. 8.

As best shown in FIGS. 2 and 8, an aperture acting as an air vent 34 is contained on the cover surface 66 of the raised area near the inlet 30. The inlet 30 is formed within the raised area as a bore 31 which is typically in the form of a truncated section having its greater diameter at the outer surface of the embossed area and its narrower diameter at the point where the bore meets the open space 68. The bore 31 is configured to receive a conventional "Luer" taper (not shown).

With reference to FIGS. 5 and 7, defined within the space 68 on the cover surface 66, near the air vent 34, is a recessed ring-like surface 72, typically shaped like a square to receive the hydrophobic filter 18. The filter is typically a commercially available 0.2 micron rated hydrophobic filter. The filter resists the flow of liquid but allows air or gas to pass through, and therefore will allow any entrained air in the liquid to be vented to the outside atmosphere through the air vent 34. Like the prefilter, the hydrophobic filter 18 is secured within the ring surface 72 so that no leaks are present at the interface between the two elements. Once again, it has been found advantageous to employ ultrasonic welding in order to secure the perimeter of the filter 18 to the ring surface 72.

The second main body portion 14 is depicted in FIGS. 3, 6 and 11–14. With reference to its orientation in FIG. 11, the second body part 14, which is also made of a suitable clear plastic, comprises a generally elongated rectangular shaped structure which contains an inner surface 80 and an outer surface 82. The inner surface, in turn, contains a projection 85 which circumscribes the entire periphery of the inner surface so as to leave a recessed margin 84 which likewise circumscribes the entire periphery of the inner surface 80. The projection 85 when viewed in cross section contains a top flat surface 86, a side wall 88, and a side wall 90, which is greater in height than side wall 88. The projection 85 is positioned about the periphery of the inner surface 80 so that the recessed margin 84 mates with the top surface 48 of the projection 44 on the inner surface of the first body part 12 when the two body parts are joined together by ultrasonic welding. The top surface 86 of projection 85 also terminates in an energy director 87 centrally located about the entire top surface 86. The energy director 87, when viewed in cross-section, is an equilateral triangle with its base in the plane of top surface 86.

The outer surface 82 contains a raised area 92 which is defined by side walls 94 and 96, outlet wall 98, and cover surface 100. As can be seen with reference to FIG. 13, the two side walls 94 and 96 merge with the cover surface 100 by deviating from planarity in a smooth and continuous fashion. The cover surface 100, in turn, is slightly concave in the transverse direction, and gradually tapers as it spans from the side wall 98, located on one side of the rectangular structure, toward the other side of the rectangular structure. The concave structure is employed to facilitate placement of the filter 10 on the arm of a patient.

Figure 11:
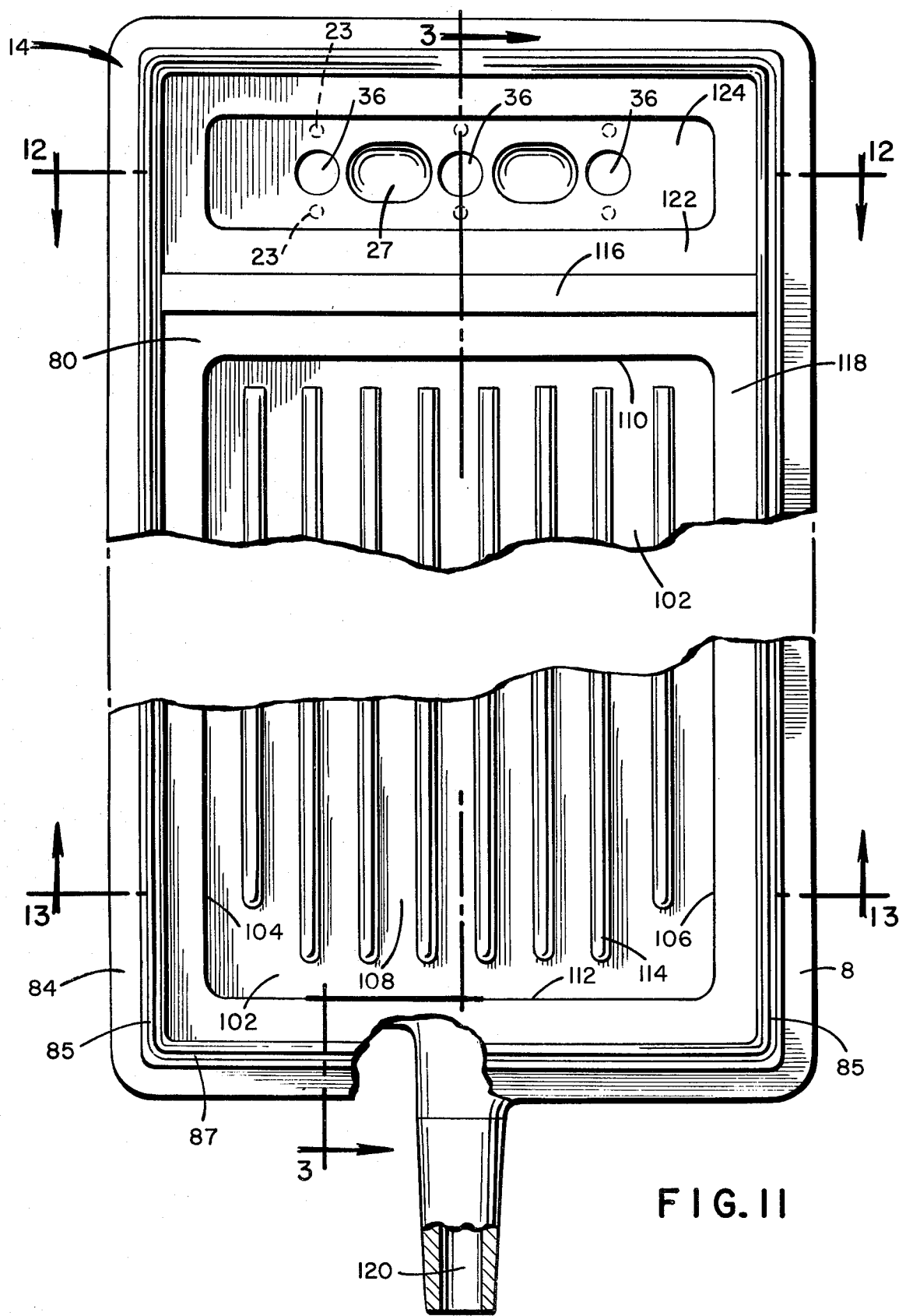
FIG. 11 is a plan view similar to FIG. 6, but with the filters removed.
Figure 12:
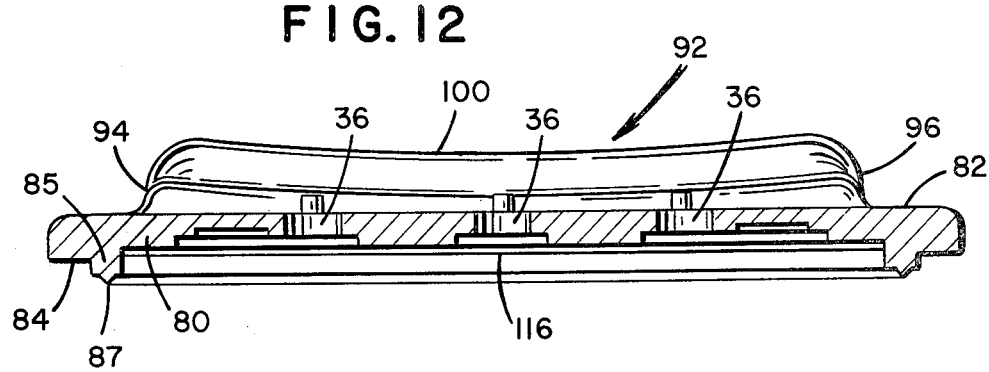
FIG. 12 is a sectional view taken along lines 12—12 of FIG. 11.
Figure 13:
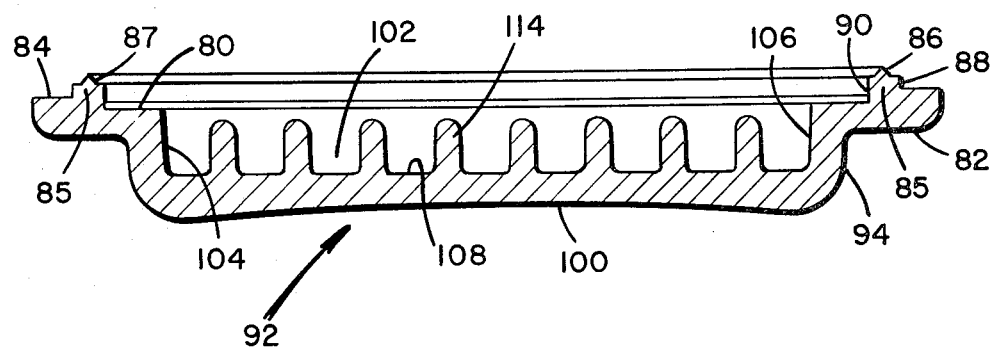
FIG. 13 is a sectional view taken along lines 13—13 of FIG. 11.
Figure 14:
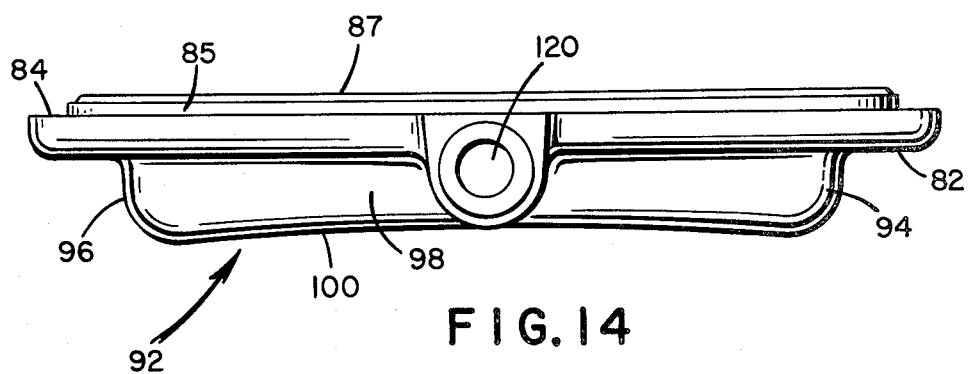
FIG. 14 is an end view of the outlet side of the half shown in FIG. 11.

As shown in FIGS. 11 and 13, the embossed area 92, also, defines an open space 102 within the inner surface 80. The open space 102 is defined by side walls 104 and 106, inner wall 108, top wall 110, and bottom wall 112, all forming part of the raised area 92. As can be seen in FIG. 3, top wall 110 is much shorter than bottom wall 112 thus imparting a tapered dimension to the length of the open space 102. The reasons for this tapered structure are to keep the volume within the space 102 as small as possible and to promote maximum flow characteristics.

Defined on inner wall 108 are a plurality of longitudinally extending ridges 114 which are in a spaced relationship. In use, the ridges on the inner surface serve to prevent the hydrophilic filter 25 from blocking itself. In some instances, when upstream pressure is too great, the hydrophilic filter 25 could be forced against the inner wall 108. The ridges 114 support the filter in the open space 102 and eliminate this blocking problem.

A transverse raised band 116 extends across the full width of the inner surface 80 from one side of projection 85 to the other in order to provide a ring-like surface 118 within the inner surface 80. The ring-like structure 118 is continuous about the open space 102 and borders on the projection 85, on three sides, and on the raised band 116, on the other side. The perimeter of the hydrophilic filter 25 is secured to the ring surface 118 in a leak resistant manner, such as by ultrasonic welding. The hydrophilic filter 25 is typically formed from a commercially available 0.2 micron filter material which allows liquid to pass through but does not permit the passage of air or the passage of bacteria or the passage of other particles larger than 0.2 microns in size. This filter element provides the primary function of sterile filtration.

With the hydrophilic filter 25 secured on the ring surface 118, the open space 102 now defines the third chamber 28. Centrally located at the bottom of the second body part 14 is a conduit 120 which extends a sufficient distance away from the bottom of the body part to receive a flexible I.V. tube, or the like. The conduit 120 contains a cylindrical bore which defines the inlet 32 providing a fluid passageway from the third chamber 28 to the exterior of the conduit.

As shown in FIG. 11, the raised band 116 defines a surface 122 which is in the form of a ring, the inner portion of which surrounds another recessed area 124, and the outer portion of which is defined on three sides by the projection 85 and on the fourth side by the raised band 116. Like the previous ring surfaces, ring surface 122 receives a second hydrophobic filter 20, the perimeter of which is secured to the ring surface in a leak proof manner, such as by ultrasonic welding. The filter 20 is typically made of a 0.2 micron rated hydrophobic filter material, which resists the flow of liquid but allows air or gas to pass through, and thus allows any entrained air in the liquid to be vented to the outside atmosphere through vent apertures 36.

To complete the structure of the filter assembly 10, the two body parts 12 and 14, just described in great detail, are joined or fused together through the mating of the top surface 48 of projection 44 with the recessed margin 84 in a leak proof manner such as by ultrasonic welding to thereby define the second chamber 26 as shown in FIG. 4. The volume of the second chamber 26 is chosen to be as small as possible while still maintaining proper fluid flow.

Figure 15:
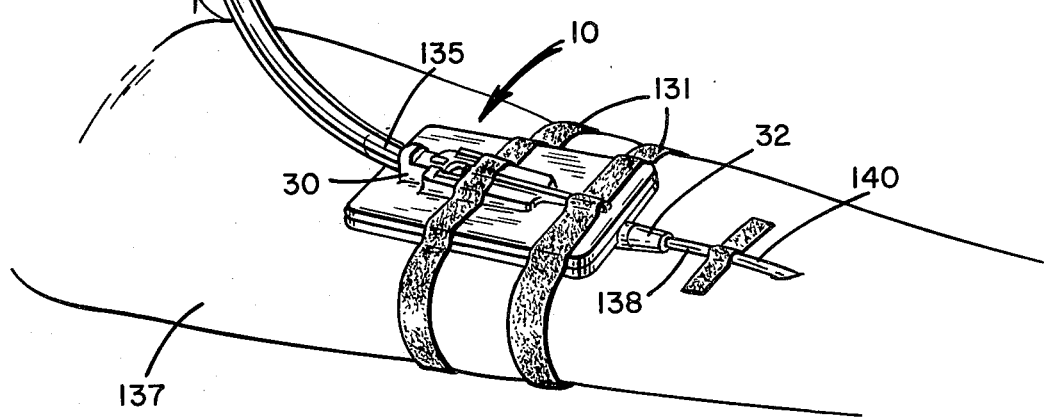
FIG. 15 is a schematic view showing the filter assembly in a I.V. Set.

With reference to FIG. 15 there is presented a schematic diagram showing the filter in a position of intended use connected to the basic elements for the intravenous administration of parenteral solution. A container 130 of parential solution 132 is suspended in the usual manner above the filter unit 10. A conventional hookup 134 connects a flexible tubing 136 to the source of parenteral solution 130. The other end of the flexible tubing 136 is connected to the inlet 30 of the filter 10 in a conventional air tight manner through the use of a Luer taper 135. Meanwhile, the filter 10, is secured to the arm 137 of the patient by wrapping a conventional surgical tape 131 about the filter 10 and the arm 137 of the patient. It is also contemplated to mount the filter 10 at any other location on the patient's body where intravenous feeding is normally applied, such as, to the leg of the patient with the outlet 32 facing the foot. As best shown in FIG. 16, the series of pegs 23 and pair of oval projections 27 prevent the air vents 34 from being blocked by the skin of the patient. Finally, it is also contemplated that the filter 10 may be free-hanging within the intravenous system in an orientation similar to that shown in FIG. 1.

As best seen in FIG. 8, the air vent 34 is surrounded by four raised portions 55 which are arranged to provide spaces 57. Should any of the tape 131 be placed over the air vent 34, the raised portions 55 suspend the tape over the spaces 57, thus providing a clear passageway for air escaping from the air vent 34 to the atmosphere.

A lower flexible tubing 138 is secured to the outlet 32 of the filter 10, again in a conventional air tight manner. The lower end of the flexible tubing 138 terminates in a cannula or needle 140 for insertion into the arm of the patient for administration of the parenteral solution.

With reference to FIG. 4, the parenteral fluid 132, entrained with air, enters the inlet 30, which provides a fluid passageway into the first chamber 24. As chamber 24 fills with the fluid 132, the air entrained in the fluid rises and is expelled to the atmosphere by passing through hydrophobic filter 18 and the associated vent 34. The fluid 132 in chamber 24 then passes to the second chamber 26 by way of the prefilter 22. It should be pointed out that the prefilter is used to prevent passage of particulate matter, but does not prevent passage of the fluid as well as the air contained within the fluid.

As the second chamber 26 fills with fluid 132, any of the remaining air rises within chamber 26 and is vented to the atmosphere by passing through hydrophobic filter 20 and air vents 36. The fluid 132 in chamber 26 then passes to chamber 28 by way of hydrophilic filter 24. This filter allows the fluid to pass but prevents any air and bacteria from passing into the third chamber 28. The fluid in chamber 28, after passing through chambers 24 and 26 is now free of air, particulate matter and bacteria. The filered fluid 132 in chamber 28 now passes through the outlet 32 into the flexible tubing 138 for eventual administration into the patient. It is to be understood that after priming, most of the entrained air is eliminated when the inlet stream flows across the hydrophobic filter 18.

Although the present invention has been shown and described in terms of a specific preferred embodiment, it will be appreciated by those skilled in the art that changes or modifications are possible which do not depart from the inventive concepts described and taught herein. Such changes and modifications are deemed to fall within the purview of these inventive concepts. In addition, it is contemplated that the filter assembly may be employed in an environment other than intravenous therapy. A fluid system in which gas and particulate matter must be removed can benefit from the use of a filter assembly embodying the teachings of the present invention.

What is claimed is:

1. A filter assembly for removing particulate matter, bacteria, and air from a liquid, said filter assembly comprising:
    a housing having first, second, and third chambers;
    inlet means for receiving said liquid containing air in said first chamber;
    first venting means for venting said air in said first chamber to the atmosphere;
    passage means providing a fluid passage from said first chamber to said second chamber;
    prefilter means for preventing particulate matter in said liquid from entering said second chamber;
    second venting means for venting to the atmosphere the air entering said second chamber;
    means providing a fluid passage from said second chamber to said third chamber;
    bacteria filtering means for preventing air and bacteria in said second chamber from entering said third chamber; and
    outlet means for providing an exit for the liquid in said third chamber.

2. The filter assembly of claim 1, wherein said housing comprises first and second body parts, said first chamber being defined in said first body part, said third chamber being defined in said second body part, said second chamber being defined when said first and second body parts are joined together.

3. The filter assembly of claim 1, wherein said inlet means is adapted to receive a Luer taper.

4. The filter assembly of claim 1, wherein each of said first and second venting means comprises a hydrophobic filter and a vent aperture in said housing, said vent aperture for allowing air to pass from said hydrophobic filter to the atmosphere.

5. The filter assembly of claim 4 wherein the hydrophobic filter of each of said first and second venting means has a lower yielded strength than said bacteria filtering means.

6. The filter assembly of claim 1, wherein said prefilter means comprises a depth filter.

7. The filter assembly of claim 1, wherein said bacteria filtering means comprises a hydrophilic filter.

8. A filter assembly for removing particulate matter, bacteria and air from a liquid, said filter assembly comprising:
   first and second body parts;
   first and second filters, each for allowing air but not liquid, to pass therethrough;
   a third filter for allowing liquid, but not air, to pass therethrough;
   a fourth filter for allowing liquid and air, but not particulate matter, to pass therethrough;
   said first filter, said fourth filter and said first body part defining a first chamber;
   said third filter and said second body part defining a second chamber;
   said second, third and fourth filters, and said first and second body parts defining a third chamber;
   said first chamber being in fluid communication with said third chamber via said fourth filter and being in communication with the atmosphere via said first filter;
   said third chamber being in fluid communication with said second chamber via said third filter and being in communication with the atmosphere via said second filter;
   inlet means for receiving said liquid containing particulate matter, bacteria and air in said first chamber; and
   outlet means for providing an exit for liquid in said second chamber.

9. A filter assembly for removing particulate matter, bacteria and air from a liquid, said filter assembly comprising:
   a housing;
   first, second, and third chambers defined within the interior of said housing;
   an inlet means for introducing said liquid into said first chamber;
   first filter means in said housing and defining a first portion of said first chamber for allowing air, but not liquid, to pass from said first chamber to the exterior of the housing;
   second filter means, in said housing, and defining a second portion of said first chamber and a first portion of said second chamber for filtering particulate matter and allowing said liquid to pass to said second chamber;
   third filter means, in said housing and defining a second portion of said second chamber for allowing air, but not liquid, to pass from said second chamber to the exterior of the housing;
   fourth filter means, in said housing and defining a third portion of said second chamber and a first portion of said third chamber for allowing liquid, but not air, to pass to said third chamber; and
   outlet means for providing a exit for liquid in said third chamber.

10. A filter assembly for removing particulate matter, bacteria and air from a liquid, said filter assembly comprising:
    a housing;
    an inlet means for receiving the liquid within said housing;
    an outlet means for providing an exit for the liquid in said housing;
    a primary filtration stage disposed within said housing so that all liquid entering said inlet means passes through said primary filtration stage, said primary filtration stage including filter means for removing particulate matter from said liquid;
    a secondary filtration stage disposed within said housing so that all liquid leaving said primary filtration stage passes through said secondary filtration stage before passing through said outlet means, said secondary filtration stage including means for removing bacteria from said liquid and for preventing air from passing through said secondary filtration stage to said outlet means; and
    air vent means for venting to the atmosphere air contained in the liquid passing through each of said primary and secondary filtration stages.

11. The filter assembly of claim 10, wherein said primary filtration stage comprises a hydrophobic filter for venting air in said liquid to the atmosphere.

12. The filter assembly of claim 10, wherein said filter means comprises a depth filter.

13. The filter assembly of claim 10, wherein said secondary filtration stage comprises a hydrophobic filter for venting air in said liquid to the atmosphere.

14. The filter assembly of claim 10, wherein said means for removing bacteria comprises a hydrophilic filter.

15. A filter assembly for removing particulate matter, bacteria, and air from a liquid, said filter assembly comprising:
    a housing;
    inlet means for receiving liquid within said housing;
    first air vent means for venting air to the atmosphere that is contained within the liquid;
    prefilter means within said housing for filtering particulate matter from said liquid following removal of air from the liquid by said first air vent means;
    second air vent means for venting air to the atmosphere from the liquid passing through said prefilter means;
    bacteria filtering means disposed within said housing for filtering bacteria and blocking the passage of air from said liquid following removal of air from the liquid by said second air vent means; and
    outlet means for providing a exit for said liquid after passage through said bacteria filtering means.

* * * * *